US010167435B2

United States Patent
Amblard et al.

(10) Patent No.: US 10,167,435 B2
(45) Date of Patent: Jan. 1, 2019

(54) LIQUID COMPOSITIONS FOR MARKING LIQUID HYDROCARBON MOTOR FUELS AND OTHER FUELS, MOTOR FUELS AND OTHER FUELS CONTAINING THEM AND PROCESS FOR DETECTING THE MARKERS

(75) Inventors: Bénédicte Amblard, Lyon (FR); Denis Fadel, Chasse sur Rhône (FR); Jean-Paul Mercier, Paris (FR); Frédéric Tort, Brignais (FR); Christian Tremoliere, Saint-Vallier-de-Thiey (FR)

(73) Assignee: Total Marketing Services, Puteaux (FR)

( * ) Notice: Subject to any disclaimer, the term of this patent is extended or adjusted under 35 U.S.C. 154(b) by 347 days.

(21) Appl. No.: 13/983,728

(22) PCT Filed: Feb. 7, 2012

(86) PCT No.: PCT/EP2012/052067
§ 371 (c)(1),
(2), (4) Date: Aug. 5, 2013

(87) PCT Pub. No.: WO2012/107454
PCT Pub. Date: Aug. 16, 2012

(65) Prior Publication Data
US 2013/0305596 A1 Nov. 21, 2013

(30) Foreign Application Priority Data

Feb. 8, 2011 (FR) ...................................... 11 51007

(51) Int. Cl.
| | | |
|---|---|---|
| C10L 1/188 | (2006.01) | |
| C10L 1/00 | (2006.01) | |
| C10L 1/19 | (2006.01) | |
| G01N 30/02 | (2006.01) | |
| G01N 30/72 | (2006.01) | |

(52) U.S. Cl.
CPC ............ C10L 1/188 (2013.01); C10L 1/003 (2013.01); C10L 1/19 (2013.01); G01N 30/02 (2013.01); G01N 30/7206 (2013.01)

(58) Field of Classification Search
CPC . C10L 1/003; C10L 1/188; C10L 1/19; G01N 30/02; G01N 30/7206
USPC ................. 44/411; 73/23.35, 23.37
See application file for complete search history.

(56) References Cited

U.S. PATENT DOCUMENTS

| | | |
|---|---|---|
| 3,862,120 A | 1/1975 | Orelup |
| 4,141,692 A | 2/1979 | Keller |
| 4,209,302 A | 6/1980 | Orelup |
| 4,511,369 A | 4/1985 | Denis et al. |
| 4,652,273 A | 3/1987 | Maldonado et al. |
| 4,664,676 A | 5/1987 | Denis et al. |
| 4,731,095 A | 3/1988 | Garapon et al. |
| 4,900,332 A | 2/1990 | Denis et al. |
| 5,106,515 A | 4/1992 | Denis et al. |
| 5,234,475 A | 8/1993 | Malhotra et al. |
| 5,256,740 A | 10/1993 | Denis et al. |
| 5,449,386 A | 9/1995 | Denis et al. |
| 5,456,730 A | 10/1995 | Hart et al. |
| 5,730,029 A | 3/1998 | Stoldt et al. |
| 5,984,983 A * | 11/1999 | Asgaonkar ............... C10L 1/003 44/385 |
| 5,998,530 A | 12/1999 | Krull et al. |
| 6,043,201 A | 3/2000 | Milbrath et al. |
| 6,071,318 A | 6/2000 | Mallet et al. |
| 6,461,421 B1 | 10/2002 | Ronvak |
| 6,511,520 B1 | 1/2003 | Eber et al. |
| 7,374,589 B2 | 5/2008 | Bernasconi et al. |
| 8,252,594 B2 | 8/2012 | Banavali et al. |
| 2005/0223631 A1 | 10/2005 | Jackson |
| 2005/0245407 A1 | 11/2005 | Ishihara et al. |
| 2007/0149415 A1 | 6/2007 | Ebert et al. |
| 2008/0096790 A1 | 4/2008 | Behan et al. |
| 2009/0253612 A1 | 10/2009 | Mushock et al. |
| 2011/0130323 A1 | 6/2011 | Behan et al. |

FOREIGN PATENT DOCUMENTS

| | | | |
|---|---|---|---|
| CA | 1321444 C | 8/1993 | |
| CA | 2145168 A1 | 3/1994 | |
| CA | 2146573 A1 | 6/1994 | |
| CA | 2154344 A1 | 8/1994 | |
| CA | 2236322 A1 | 5/1997 | |
| CN | 101412933 A * | 4/2009 | |
| EP | 0261959 A2 | 3/1988 | |
| EP | 512404 A1 * | 11/1992 | |
| EP | 0512404 A1 | 11/1992 | |
| EP | 0512404 A1 * | 11/1992 | ........ C10M 171/007 |
| EP | 0736590 A2 | 10/1996 | |
| EP | 1484385 A1 * | 12/2004 | ............. C10L 1/026 |

(Continued)

OTHER PUBLICATIONS

CN 101412933 A Translation.*

Primary Examiner — Latosha Hines
(74) Attorney, Agent, or Firm — Harness, Dickey & Pierce, PLC

(57) ABSTRACT

The present disclosure includes liquid compositions that can be used for marking liquid hydrocarbon-based fuels and combustibles; these compositions include at least one marker, one or more solvents and, optionally, one or more functional additives other than the markers. The disclosure also includes a process for qualitative and quantitative detection of these markers present in a liquid hydrocarbon-based composition.

16 Claims, No Drawings

(56) References Cited

FOREIGN PATENT DOCUMENTS

| EP | 1484385 | A1 | 12/2004 | |
|---|---|---|---|---|
| EP | 1591514 | A2 | 11/2005 | |
| EP | 1591514 | A2 * | 11/2005 | ............. C10L 1/143 |
| FR | 2528423 | A1 | 12/1983 | |
| FR | 2772783 | A1 | 6/1999 | |
| GB | 2121808 | A | 1/1984 | |
| WO | WO-9314178 | A1 | 7/1993 | |
| WO | WO-2010039152 | A1 | 4/2010 | |

* cited by examiner

LIQUID COMPOSITIONS FOR MARKING LIQUID HYDROCARBON MOTOR FUELS AND OTHER FUELS, MOTOR FUELS AND OTHER FUELS CONTAINING THEM AND PROCESS FOR DETECTING THE MARKERS

CROSS-REFERENCE TO RELATED APPLICATIONS

This application is a National Phase Entry of International Application No. PCT/EP2012/052067, filed on Feb. 7, 2012, which claims priority to French Patent Application Serial No. 1151007, filed on Feb. 8, 2011, both of which are incorporated by reference herein.

TECHNICAL FIELD

This invention relates to the use of specific chemical compounds as markers of liquid hydrocarbon products or liquid hydrocarbons, such as motor fuels and other liquid hydrocarbon fuels, crude oil. These markers can be used either directly in the hydrocarbon product, or via a package of additives which is then incorporated in the motor fuel or other fuel. These markers are intended to mark the liquid hydrocarbon so that it can be rapidly identified with respect to its source, its integrity, and in particular that of the additives which are incorporated. When the chemical markers are mixed beforehand with one or more additives (commonly called "package of additives" in the profession) they allow the identification of the type and quantity of the package incorporated in the liquid hydrocarbon.

BACKGROUND

Numerous techniques have been used to mark liquid hydrocarbon products with the aim of identifying their source and their integrity; they typically involve the incorporation of small quantities of additives or markers in the hydrocarbon. The detection of the markers can be carried out by a certain number of standard analytical techniques such as colorimetry, IR, UV or UV-Visible spectroscopy, mass spectrometry, atomic adsorption spectrometry, gas chromatography and/or liquid chromatography (some of these detection and analysis techniques being optionally coupled together). When a liquid hydrocarbon such as crude oil, an oil base originating from the refinery, a motor fuel or other fuel, containing a marker is accidentally spilt into the environment (for example hydrocarbons leaking from storage tanks, service-station tanks, pipelines etc.), the detection of the marker allows identification of the source of the hydrocarbon.

Moreover, the presence and the concentration of the additives for improving performance incorporated in the motor fuels and other fuels can be deduced by measuring the concentration of the marker added to either the motor fuel or other fuel, or to the additive or package of additives. The marked motor fuel or other hydrocarbon fuel can be checked throughout its distribution network in order to verify its integrity. It can thus be ensured that the motor fuel or other fuel has not been subject to contamination or dilution with other liquid hydrocarbons, which also makes it possible to verify that there is no under- or overdosing of the commercial motor fuel or other fuel with additives. When a marker is included in the package of additives in a given quantity, the concentration of the package in the motor fuel or other hydrocarbon fuel can be deduced by determining the quantity of marker in the final motor fuel or other hydrocarbon fuel by implementing a reliable and precise analysis technique.

Radioactive markers based on tritium, iodine 131, or sulphur 35 have been used for tracing crude oil and motor fuels in pipelines and in storage facilities. Essentially for tax reasons, each type of motor fuel or other fuel intended for the general public has a specific marker added to it, called a "customs tracer", which is generally a specific dye added in a quantity determined by the regulations of the marketing country.

U.S. Pat. No. 4,141,692 describes the use of chlorinated hydrocarbons having at least 3 chlorine atoms, at least two carbon atoms and an atomic ratio of Cl/C of at least 1 to 3 as hydrocarbon markers. Detection of these markers is carried out by an electron capture detector after separation by gas chromatography. The use of chlorinated hydrocarbons as markers of motor fuels and other liquid hydrocarbon fuels has drawbacks, in particular a certain toxicity (chlorine gas release and/or increased emissions of chlorinated hydrocarbons potentially generating greenhouse gases).

U.S. Pat. No. 4,209,302 describes the use of 1-(4-morpholino)-3-(alpha or beta-naphthylamino) propane at a rate of 0.5 to 12 ppm as marker for gasoline-type motor fuels. These markers do not dye the gasoline; in order to detect them, it is necessary to carry out a chemical extraction followed by a treatment with diazotized 2-chloro-4-nitroaniline which leads to a pink-coloured solution, a colour that can be measured by colorimetry. The major drawback of this detection technique is the preliminary chemical extraction step which can lead to increased measurement errors.

FR Patent No. 2 212 390 or U.S. Pat. No. 3,862,120 describe diazo dyes for liquids which are not miscible with water, in particular the petroleum motor fuels and a process making it possible to quantitatively detect their presence in said liquids by IR adsorption or by thin layer chromatography. U.S. Pat. No. 5,234,475 proposes using as markers of liquid hydrocarbons (gasoline, diesel, jet fuel etc.) one or more fullerenes in quantities ranging from 0.01 to 100 ppm, which can be detected by mass or UV-visible spectroscopy. As the manufacture of the fullerenes is not currently really possible on an industrial scale, these molecules are much too expensive to be incorporated in motor fuels and other convenience fuels intended for the general public.

EP Patent No. 512 404 describes the use, as markers of liquid hydrocarbons, of chemical compounds having an aromatic ring substituted by 2 $NO_2$ groups and an amide or ester group which can be detected by gas chromatography. These markers can be incorporated into the motor fuel directly or via the package of additives. These compounds are hydrolyzed in the presence of traces of water in the hydrocarbon, rendering their use unreliable for the marking and precise quantitative detection of the motor fuel.

EP Patent No. 1 699 907 describes packages of additives for motor fuels or lubricants which comprise anthraquinone derivatives as markers and the use of these packages in motor fuels and lubricants. EP Patent No. 1 816 181 describes markers for ethanol motor fuels which are substituted aromatic compounds, having an axis of three-fold symmetry and containing N, O, P, B which can preferably be used between 0.01 ppm and 50 ppm by mass in ethanol motor fuels. WO 2010/039152 describes a process for marking motor fuels for authentification, in order to ensure, for example, their origin and/or optional mixtures or dilutions. The chemical nature of the markers is not described in detail; it is only indicated that the markers can be dyes or non-radioactive isotopes.

U.S. Pat. No. 5,984,983 describes the use of carbonyl compounds as markers of motor fuels. These markers can be chosen from ketones, aldehydes, esters including lactones), amides (including lactames and imides, anhydrides and carboxylic acids). The presence of these markers is detected by the IR absorption of the carbonyl functions. The only example relates to a gasoline motor fuel marked with dibutyl phthalate (absorbance peak 1740 cm$^{-1}$) and acetophenone (absorbance peak 1700 cm$^{-1}$).

SUMMARY

The present invention relates to a liquid composition comprising:
a) at least one marker, chosen from the following aliphatic or cycloaliphatic compounds:
   tricyclodecenyl isobutyrate (3a,4,5,6,7,7a-hexahydro-4,7-methano-1h-inden-5 (or 6)-yl) (CAS 67634-20-2)
   tricyclodecenyl propionate (CAS 17511-60-3)
   cis-3-hexenyl acetate (CAS 3681-71-8)
   ethyl linalool (CAS 10339-55-6)
   prenyl acetate (CAS 1191-16-8)
   ethyl myristate (CAS 124-06-1)
   para-tert-butylcyclohexyl acetate (CAS 32210-23-4)
   butyl acetate (CAS 123-86-4),
   tricyclodecenyl acetate (4,7-methano-1h-inden-6-ol, 3a,4,5,6,7,7a-hexahydro-) (CAS 5413-60-5)
   ethyl caprate (CAS 110-38-3)
b) a solvent or a mixture of solvents,
c) one or more functional additives for motor fuels and/or liquid hydrocarbon fuels, making it possible to improve the performances of the motor fuel or other fuel.

A subject of the present invention is also the use of this liquid composition as a package of additives for motor fuels or liquid hydrocarbon fuels as well as a method for analyzing the liquid hydrocarbon product comprising as an additive said package of additives, by detection and quantitative analysis of the marker or markers a) contained in the motor fuel or other liquid fuel.

DETAILED DESCRIPTION

The present invention relates to a liquid composition comprising
a) at least one marker, preferably at least 2, chosen from the following aliphatic or cycloaliphatic compounds:
   tricyclodecenyl isobutyrate (3a,4,5,6,7,7a-hexahydro-4,7-methano-1h-inden-5 (or 6)-yl) (CAS 67634-20-2)
   tricyclodecenyl propionate (CAS 17511-60-3)
   cis-3-hexenyl acetate (CAS 3681-71-8)
   ethyl linalool (CAS 10339-55-6)
   prenyl acetate (CAS 1191-16-8)
   ethyl myristate (CAS 124-06-1)
   para-tert-butylcyclohexyl acetate (CAS 32210-23-4)
   butyl acetate (CAS 123-86-4),
   tricyclodecenyl acetate (4,7-methano-1h-inden-6-ol, 3a,4,5,6,7,7a-hexahydro-) (CAS 5413-60-5)
   ethyl caprate(CAS 110-38-3)
b) a solvent or a mixture of solvents,
c) optionally one or more functional additives for motor fuels and/or liquid hydrocarbon fuels, chosen from the detergents, dispersants etc.

The markers a) for liquid hydrocarbon compositions defined above satisfy the following conditions:

having sufficient stability under the usual conditions of use of the liquid hydrocarbon composition,
maintaining the physico-chemical properties of the motor fuel or other fuel,
being compatible with the components of the package of additives and with those of the motor fuel and other fuel
having sufficient stability to be able to be used in the form of concentrated solutions,
being able to be used in a low quantity and be detectable by simple, rapid, precise and reliable detection techniques,
being distinct from the regulation and legal markers.

Advantageously, certain of the markers a) defined above, apart from the abovementioned marking properties, exhibit additional properties or performances; this is for example the case with 3a,4,5,6,7,7a-hexahydro-4,7-methano-1h-inden-5 (or 6)-yl isobutyrate, tricyclodecenyl propionate and 4,7-methano-1h-inden-6-ol, 3a,4,5,6,7,7a-hexahydro-, acetate which improve the odour and/or bactericidal properties of the motor fuels and other fuels in which they are incorporated, see for example EP Patent No. 1 591 514; butyl acetate, ethyl linalool also have aromatic properties, see for example WO 01/363544 and U.S. Patent Publication No. 2008/096790.

The marker (or markers) a) is added in a sufficient quantity to ensure its detection, and preferably its quantification after it has been added to the motor fuel or other fuel. Typically each marker a) is added at a concentration generally ranging from 1 to 500 parts per million by mass (ppm m/m) relative to the total mass of motor fuel or other liquid hydrocarbon fuel containing additives, and preferably in a concentration ranging from 1 to 50 ppm m/m. Typically, the minimum detection threshold of these markers a) is generally 1 ppm m/m for a qualitative detection (i.e. making it possible to identify the presence of the marker a) and from 2 to 3 ppm m/m for a quantitative detection. The solvent (or solvents) b) in which the marker or markers a) and any other additives c) of the liquid composition are soluble, generally comprise aliphatic and/or aromatic hydrocarbons or mixtures of hydrocarbons, for example fractions of gasoline, kerosene, decane, pentadecane, toluene, xylene, and/or ethylbenzene and/or mixtures of commercial solvents such as for example Solvarex 10, Solvarex LN, Solvent Naphtha, Shellsol AB, Shellsol D, Solvesso 150, Solvesso 150 ND, Solvesso 200, Exxsol, ISOPAR and optionally polar dissolution adjuvants, such as 2-ethylhexanol, decanol, isodecanol and/or isotridecanol.

In a non-exhaustive manner, the functional additive or additives c) can be chosen from:
combustion-improving additives; for the gasoil-type motor fuels, there can be mentioned the procetane additives, in particular (but not limitatively) chosen from the alkyl nitrates, preferably 2-ethyl hexyl nitrate, the aroyl peroxides, preferably benzyl peroxide, and the alkyl peroxides, preferably di-tert-butyl peroxide; for the gasoline-type motor fuels, there can be mentioned the additives improving the octane rating; for the fuels such as domestic heating oil, heavy fuel oil, marine fuel oil, there can be mentioned methylcyclopentadienyl manganese tricarbonyl (MMT);
anti-oxidant additives, such as aliphatic, aromatic amines, hindered phenols, such as BHT, BHQ;
demulsifiers;
anti-static or conductivity-improving additives;
dyes;
anti-foam additives, in particular (but not limitatively) chosen for example from the polysiloxanes, oxyalkylated polysiloxanes, and amides of fatty acids originating from vegetable or animal oils; examples of such additives are given in EP Patent No. 861 182, EP Patent No. 663,000, EP Patent No. 736 590;

detergent or dispersant additives, in particular (but not imitatively) chosen from the group constituted by the amines, succinimides, succinamides, alkenylsuccinimides, polyalkylamines, polyalkyl polyamines, polyetheramines, Mannich bases; examples of such additives are given in EP Patent No. 938 535;

anti-corrosion additives such as ammonium salts of carboxylic acids;

chelating agents and/or sequestrating agents of metals, such as triazoles, disalicylidene alkylene diamines, and in particular N,N' bis(salicydene)propane diamine;

lubricity additives, anti-wear agents and/or friction modifiers, in particular (but not limitatively) chosen from the group constituted by the fatty acids and their ester or amide derivatives, in particular glycerol monooleate, and the derivatives of mono- and polycyclic carboxylic acids; examples of such additives are given in the following documents: EP Patent No. 680 506, EP Patent No. 860 494, WO 98/04656, EP Patent No. 915 944, FR Patent No. 2 772 783, FR Patent No. 2 772 784;

low temperature behaviour additives and in particular additives improving the cloud point, in particular (but not limitatively) chosen from the group constituted by the long-chain olefin/(meth)acrylic ester/maleimide terpolymers, and fumaric/maleic acid ester polymers. Examples of such additives are given in EP Patent No. 71 513, EP Patent No. 100 248, FR Patent No. 2 528 051, FR Patent No. 2 528 423, EP Patent No. 1 121 95, EP Patent No. 1 727 58, EP Patent No. 271 385, EP Patent No. 2 913 67; anti-settling additives and/or wax dispersants in particular (but not limitatively) chosen from the group constituted by (meth)acrylic acid/polyamine-amidified alkyl(meth)acrylate copolymers, polyamine alkenyl succinimides, the derivatives of phthalamic acid and of double-chain fatty amine; alkyl phenol/aldehyde resins; examples of such additives are given in EP Patent No. 261 959, EP Patent No. 593 331, EP Patent No. 674 689, EP Patent No. 327 423, EP Patent No. 512 889, EP Patent No. 832 172; U.S. Patent Publication No. 2005/0223631; U.S. Pat. No. 5,998, 530; WO 93/14178; the cold operability multi-functional additives chosen from the group constituted by the polymers based on olefin and alkenyl nitrate as described in EP Patent No. 573 490;

other additives improving low temperature behaviour and filterability (CFI), such as EVA and/or EVP copolymers;

metal passivators, such as triazoles, alkylated benzotriazoles;

acidity neutralizers such as cyclic alkylamines;

markers other than those corresponding to the definition of the markers a) and in particular the markers required by the regulations, for example the dyes specific to each type of motor fuel or other fuel.

The functional additives c) are generally added to the liquid hydrocarbon composition (motor fuel or other fuel) in quantities ranging from 5 to 1,000 ppm via at least one liquid composition according to the invention and/or incorporated via another package of additives and/or directly to the hydrocarbon composition.

The present invention also relates to the use of at least one liquid composition as defined above as a package of additives for motor fuels and other liquid hydrocarbon fuels as well as for lubricating oils. The motor fuels and other liquid hydrocarbon fuels comprise middle distillates with a boiling point comprised between 100 and 500° C.; their incipient crystallization temperature ICT is often greater than or equal to −20° C., generally comprised between −15° C. and +10° C. These distillates are mixtures of bases which can be chosen for example from the distillates obtained by direct distillation of petroleum or crude hydrocarbons, vacuum distillates, hydrotreated distillates, distillates originating from the catalytic cracking and/or hydrocracking of vacuum distillates, distillates resulting from ARDS (atmospheric residue desulphurization)-type conversion processes and/or visbreaking. The motor fuels and other liquid fuels can also contain light cuts such as the gasolines originating from distillation, catalytic or thermal cracking units, isomerization alkylation units, desulphurization units and steam cracking units.

The motor fuels and other fuels liquids can also contain novel sources of distillates, among which there can in particular be mentioned:

the heavier cuts originating from the cracking and visbreaking processes, with a high concentration of heavy paraffins, comprising more than 18 carbon atoms, the synthetic distillates originating from the conversion of the gas such as those originating from the Fischer Tropsch process, the synthetic distillates resulting from the treatment of biomass of vegetable and/or animal origin, such as in particular NexBTL, alone or in a mixture. The vegetable or animal biomass and the vegetable or animal oils can be hydrotreated or hydrodeoxygenated, coker gasoils, alcohols, such as methanol, ethanol, butanols, ethers, (MTBE, ETBE etc.) generally used in a mixture with gasoline motor fuels, but sometimes with heavier gasoil-type motor fuels, vegetable and/or animal oils and/or their esters, such as methyl or ethyl esters of vegetable oils (MEVO, EEVO), hydrotreated and/or hydrocracked and/or hydrodeoxygenated (HDO) vegetable and/or animal oils and/or also biodiesels of animal and/or vegetable origin.

These novel motor fuel bases can be used alone or in a mixture with standard petroleum middle distillates as a motor fuel base and/or other fuel base; they generally comprise long paraffin chains greater than or equal to 10 carbon atoms and preferably from C14 to C30. Generally, the sulphur content of the motor fuels and other liquid hydrocarbon fuels containing additives ready for use is less than 5,000 ppm m/m, preferably less than 500 ppm m/m, and more preferentially less than 50 ppm m/m, or even less than 10 ppm m/m, and advantageously without sulphur, in particular for the gasoil- and jet-type motor fuels. For distillates of the domestic heating oil type the sulphur content is less than 1,000 ppm m/m.

The motor fuels and other liquid hydrocarbon fuels can be commercial products, in particular:

gasoline motor fuels the boiling point of which is generally comprised between 20 and 200° C., jet motor fuels, gasoil or diesel motor fuels, domestic heating oils, heavy fuel oils the boiling point of which is comprised between 120 and 500° C., preferably 140 and 400° C.

The present invention also relates to a method for analyzing motor fuel or other liquid hydrocarbon fuel to which at least one marker a) has been added, which may or may not be contained in a liquid composition as defined previously by detection and optionally quantitative analysis of the marker or markers a) added to the motor fuel or liquid hydrocarbon fuel. The process according to the invention comprises the following steps:

analysis of a sample of liquid hydrocarbon composition containing at least one marker a) using a simple, reliable and robust analytical method, then detection of one or more markers a)

and optionally measurement of the concentration of each of the markers a) detected within the motor fuel or liquid hydrocarbon fuel.

The analytical methods for detecting the markers a) implemented in the context of the process according to the invention include, but are not limited to, gas or liquid chromatography coupled with one or more detectors of markers a) such as an electron capture detector, mass spectrometer and/or flame ionization detector.

Gas chromatography is one of the analytical methods preferred for implementing the process according to the invention; it makes it possible to separate chemical products according to their interaction with the stationary phase of the chromatography column, either at a constant given temperature, or according to a given programme of temperatures. Each chemical compound interacts differently with a given stationary phase under the given temperature condition and therefore has a given retention time under these defined conditions. Once determined, the retention time can be used to identify the marker a) whilst the peak area can be used to determine the concentration of the marker. Standard gas chromatography (GC) and multidimensional "heart-cutting"-type gas chromatography (GC-GC) coupled with a mass spectrometer (MS) are the preferred analytical methods, the multidimensional "heart-cutting"-type gas chromatography (GC-GC) which allows better separation is particularly preferred. Two-dimensional chromatography (GC*GC or GC2D) can also be mentioned, a detailed description of which is available in the article entitled "Apport de la chromatographie en phase gazeuse bidimensionnelle. Chromatographie en phase gazeuse, GC×GC, chromatographie bidimensionnelle", which can be accessed at www.spectrabiology.com/Documents/SA247_26-31.pdf.

When the analysis process according to the invention uses a method of gas phase chromatography, the stationary phases used for separating and identifying the markers a) according to the invention are generally silicone polymers derived from polysiloxane. This phase is grafted onto the silica column. The polarity of the column can be modified by substituting a phenyl or cyanopropyl group for a methyl group.

Other much more polar phases exist, based on polyethylene glycol. They are grafted onto the silica walls of the column. The columns used are generally capillary columns.

The detectors coupled with the chromatography are preferably mass spectrometry detectors. Mass spectrometry is a very sensitive and specific technique which allows detection starting from a very low content of the ions of the molecule to be assayed (typically up to 1 ppm m/m), these ions being able to be specific to the markers a) according to the invention.

The operating conditions of the multidimensional chromatography GC-GC, are generally the following:

1) injection into a 1st chromatography column, of a liquid mixture comprising a liquid hydrocarbon composition (for example a motor fuel or another liquid fuel containing the composition of additives defined above) and one or more markers a);

2) separation of the marker or markers a) and any other compounds contained in the mixture;

3) injection of the fraction into a 2nd chromatography column in order to ensure the complete separation of all the compounds, including the markers a), then passage through a mass spectrometer allowing each compound (i.e. each marker a)) to be specifically identified and optionally quantified.

The length of the 1st column is generally comprised between 5 to 60 metres, and is preferably shorter than that of the 2nd column, which generally ranges from 10 to 60 meters. The injector is maintained at a temperature sufficient to ensure the vaporization of all the compounds in the mixture; this temperature is typically comprised between 200 and 350° C. in the case of the hydrocarbon mixtures based on motor fuel or liquid fuel such as gasoline, kerosene, gasoil, heating oil, and higher in the case of lubricating oils. The analysis can be carried out at a constant temperature, this temperature being able to vary between 10° C. and 300° C. The analysis can also be carried out using the temperature programming. In this case the temperature programme will be developed for each type of sample analyzed: gasoline, gasoil etc.

EXAMPLES

Example 1

In this example, the GC-GC gas chromatography spectrum of a gasoil-type commercial motor fuel EN 590 is compared with that of the same motor fuel gasoil comprising as an additive 7 ppm m/m of 4,7-methano-1h-inden-6-ol, 3a,4,5,6,7,7a-hexahydro-, acetate (CAS 5413-60-5) (marker a)). For the motor fuel comprising marker a) as an additive, the spectrogram shows a retention peak at 23.3 min, a peak which does not exist in the case of the motor fuel containing no marker a). Using a mass spectrometer coupled with the GC-GC, a concentration of marker 4,7-methano-1h-inden-6-ol, 3a,4,5,6,7,7a-hexahydro-, acetate (CAS 5413-60-5) a) of 6.7 ppm m/m is measured (average obtained from 3 measurements; repeatability: 10%).

Example 2

In this example, the GC-GC gas chromatography spectrum of a commercial gasoline-type motor fuel EN 228 is compared with that of the same gasoline motor fuel comprising as an additive variable quantities of butyl acetate (CAS 123-86-4) (marker a)) ranging from 1 and 20 ppm m/m. For each concentration of marker a), the peak surface area is measured; all the data are compiled in the table below.

| Concentration of marker a) in the motor fuel gasoline (ppm m/m) | Peak surface area |
| --- | --- |
| 1 | 2.688 |
| 5 | 18.997 |
| 10 | 45.446 |
| 15 | 73.669 |
| 20 | 99.343 |

Starting from the data in this table, a calibration line is constructed (peak surface area=f (concentration of marker a)) which makes it possible to calculate, for a given peak surface area, the corresponding concentration of marker a)). The corresponding calibration line can be represented by the following equation:

$$Y=5175.8*x-4764.3 \quad R^2=0.9979$$

The correlation coefficient value of the line shows a good linearity over the interval considered.

Example 3

Different samples of commercial gasoil EN 590 are prepared, comprising as an additive variable quantities of 4,7-methano-1h-inden-6-ol, 3a,4,5,6,7,7a-hexahydro-, acetate (CAS 5413-60-5) (marker a)) ranging from 1 to 20 ppm m/m. For each concentration of marker a), the peak surface area is measured and a calibration line is constructed (peak surface area=f (concentration of marker a)) which can be represented by the following equation:

$$Y=0.00155*x-0.66999 \quad R^2=0.99895$$

A sample of the same commercial gasoil is also prepared to which 8.9 ppm m/m are added. This sample is then stored in a hermetically sealed flask for 3 months at ambient temperature.

After storage for 3 months, another laboratory again using GC/MS measures the content of the tracer 4,7-methano-1h-inden-6-ol, 3a,4,5,6,7,7a-hexahydro-, acetate (CAS 5413-60-5) in the sample and, using the calibration line the content of marker a) after 3 months, is equal to 8.65 ppm m/m. This example shows that the marker incorporated into the motor fuel remains perfectly detectable during this time and also remains perfectly quantifiable.

Example 4

This example relates to a hydrocarbon liquid of gasoline type EN 228 containing 2 different markers a) according to the present invention: butyl acetate (CAS 123-86-4) and ethyl caprate (CAS 110-38-3) and a method for analyzing these 2 markers by GC/MS. The motor fuel EN228 containing the 2 markers a) is analyzed by standard gas chromatography equipped with a polar capillary column and coupled with an MS detector (GC/MS).

On the basis of the chromatogram and spectrogram data compiled in the table below, the retention time can be assigned to each of the 2 markers a):

| Marker a) | Retention time |
|---|---|
| butyl acetate (CAS 123-86-4), | 7 minutes |
| ethyl caprate(CAS 110-38-3) | 27 minutes. |

It is noted that the 2 markers are perfectly distinguished from each other by their different retention time but also from the other molecules contained in the motor fuel.

Example 5

This example illustrates the use of marker a) according to the invention in a commercial gasoline of type EN 228. The marker is added via a package of additives improving the performance and is analyzed by following the procedure described in Example 4.

The marker, ethyl caprate(CAS 110-38-3) (marker a)) is incorporated in a package of commercial performance additives for motor fuel gasoline containing a polymeric detergent, a synthetic carrier oil and a mixture of demulsifying agents. The resulting package comprising as an additive the marker a) is incorporated in a commercial unleaded motor fuel gasoline EN 228 at a dose of 500 ppm mini). By standard gas chromatography analysis coupled with a mass spectrometer detector (GC/MS) according to the conditions of Example 4, the ethyl caprate (CAS 110-38-3) is detected 27 minutes after the injection. All the other components of the gasoline which can be detected by the mass spectrometer have passed through the column of chromatography either before or after the marker a), therefore with very different retention times.

The invention claimed is:

1. A process for the qualitative detection of at least one marker in a motor fuel or other liquid hydrocarbon fuel comprising:
    (a) the at least one marker, chosen from the following aliphatic or cycloaliphatic compounds:
        tricyclodecenyl isobutyrate (3a,4,5,6,7,7a-hexahydro-4,7-methano-1 h-inden-5 (or 6) -yl) (CAS 67634-20-2);
        tricyclodecenyl propionate (CAS 17511-60-3);
        cis-3- hexenyl acetate (CAS 3681-71-8);
        ethyl linalool (CAS 10339-55-6);
        prenyl acetate (CAS 1191-16-8);
        ethyl myristate (CAS 124-06-1);
        para-tert-butylcyclohexyl acetate (CAS 32210-23-4);
        tricyclodecenyl acetate (4,7-methano-1h-inden-6-ol, 3a,4,5,6,7,7a-hexahydro-) (CAS 5413-60-5);
        ethyl caprate(CAS 110-38-3),
        the at least one marker having a concentration of from 1 ppm to 20 ppm with regard to the motor fuel or other liquid hydrocarbon fuel;
    (b) a solvent or a mixture of solvents; and
    (c) one or more functional additives for motor fuels and/or other liquid hydrocarbon fuels, chosen from the detergents, dispersants, combustion improvers, anti-foaming agents, conductivity improvers, anti-corrosion additives, lubricity additives, anti-wear agents and/or friction modifiers, chelating agents and/or sequestrating agents of metals, demulsifiers, low temperature behaviour additives, metal passivators, acidity neutralizers, markers different from the markers; the process comprising the following steps:
        analyzing a sample of the motor fuel or other liquid fuel containing the at least one marker by an analytic method; and
        then detecting the at least one marker.

2. The process for the qualitative and quantitative detection according to claim 1 comprising a subsequent step of measuring the concentration of each of the markers detected within the motor fuel or other liquid hydrocarbon fuel.

3. A process of quantitative detection of at least one marker in a motor fuel or other liquid hydrocarbon fuel comprising:
    (a) the at least one marker, chosen from the following aliphatic or cycloaliphatic compounds:
        tricyclodecenyl isobutyrate (3a,4,5,6,7,7a-hexahydro-4,7-methano-1 h-inden-5 (or 6) -yl) (CAS 67634-20-2);
        tricyclodecenyl propionate (CAS 17511-60-3);
        cis-3- hexenyl acetate (CAS 3681-71-8);
        ethyl linalool (CAS 10339-55-6);
        prenyl acetate (CAS 1191-16-8);
        ethyl myristate (CAS 124-06-1);
        para-tert-butylcyclohexyl acetate (CAS 32210-23-4);

tricyclodecenyl acetate (4,7-methano-1h-inden-6-ol, 3a,4,5,6,7,7a-hexahydro-) (CAS 5413-60-5);
ethyl caprate(CAS 110-38-3),
the at least one marker having a concentration of from 1 ppm to 20 ppm with regard to the motor fuel or other liquid hydrocarbon fuel;
(b) a solvent or a mixture of solvents; and
(c) one or more functional additives for motor fuels and/or other liquid hydrocarbon fuels, chosen from the detergents, dispersants, combustion improvers, anti-foaming agents, conductivity improvers, anti-corrosion additives, lubricity additives, anti-wear agents and/or friction modifiers, chelating agents and/or sequestrating agents of metals, demulsifiers, low temperature behaviour additives, metal passivators, acidity neutralizers, markers different from the markers; the process comprising the following steps:
analysing a sample of motor fuel or other liquid fuel containing the at least one marker by an analytic method
detecting the marker or markers; and
measuring the concentration of each of the markers detected within the motor fuel or other liquid hydrocarbon fuel.

4. The process for detection of at least one marker according to claim 2 by multidimensional chromatography coupled with a mass spectrometer comprising the following steps:
(a) injection into a 1st chromatography column, of a liquid mixture comprising a liquid hydrocarbon composition containing one or more markers;
(b) separation of the marker or markers and any other compounds contained in the mixture;
(c) injection of the fraction into a 2nd chromatography column to ensure the complete separation of all the compounds, including the markers; and
(d) then passage through a mass spectrometer allowing each compound, to be specifically identified and optionally quantified.

5. The process for the qualitative detection according to claim 1, wherein the analytic method is gas chromatography.

6. The process for the qualitative detection according to claim 5, wherein the analytic method is multidimensional gas chromatography.

7. The process for the qualitative detection according to claim 1, wherein the detection is performed by mass spectrometry.

8. The process for the qualitative and quantitative detection according to claim 2, wherein the step of measuring the concentration is performed by mass spectrometry coupled with gas chromatography.

9. The process of quantitative detection according to claim 3, wherein the analytic method is gas chromatography.

10. The process of quantitative detection according to claim 9, wherein the analytic method is multidimensional gas chromatography.

11. The process of quantitative detection according to claim 3, wherein the measurement of the concentration of each of the markers detected is performed by mass spectrometry coupled with gas chromatography.

12. The process for the qualitative and quantitative detection according to claim 1, wherein the motor fuel or other liquid hydrocarbon fuel comprises from 2 to 3 ppm by mass of the markers a).

13. The process according to claim 1, wherein the analysing and the detecting are performed after the motor fuel or other liquid hydrocarbon fuel has been stored at ambient temperature for 3 months.

14. The process according to claim 3, wherein the analysing, the detecting, and the measuring are performed after the motor fuel or other liquid hydrocarbon fuel has been stored at ambient temperature for 3 months.

15. The process according to claim 1, wherein the at least one marker is chosen from the following compounds:
tricyclodecenyl isobutyrate (3a,4,5,6,7,7a-hexahydro-4,7-methano-1 h-inden-5 (or 6) -yl) (CAS 67634-20-2);
tricyclodecenyl propionate (CAS 17511-60-3);
cis-3- hexenyl acetate (CAS 3681-71-8);
ethyl linalool (CAS 10339-55-6);
prenyl acetate (CAS 1191-16-8);
ethyl myristate (CAS 124-06-1); and
para-tert-butylcyclohexyl acetate (CAS 32210-23-4).

16. The process according to claim 3, wherein the at least one marker is chosen from the following compounds:
tricyclodecenyl isobutyrate (3a,4,5,6,7,7a-hexahydro-4,7-methano-1 h-inden-5 (or 6) -yl) (CAS 67634-20-2);
tricyclodecenyl propionate (CAS 17511-60-3);
cis-3- hexenyl acetate (CAS 3681-71-8);
ethyl linalool (CAS 10339-55-6);
prenyl acetate (CAS 1191-16-8);
ethyl myristate (CAS 124-06-1); and
para-tert-butylcyclohexyl acetate (CAS 32210-23-4).

* * * * *